United States Patent [19]

Kataoka et al.

[11] Patent Number: 5,728,863
[45] Date of Patent: Mar. 17, 1998

[54] PROCESS FOR PRODUCING α-L-ASPARTYL-L-PHENYLALANINE METHYL ESTER

[75] Inventors: Takehiko Kataoka; Shinichi Kishimoto; Osahiro Sato, all of Kawasaki, Japan

[73] Assignee: Ajinomoto Company, Inc., Tokyo, Japan

[21] Appl. No.: 601,673

[22] Filed: Feb. 15, 1996

Related U.S. Application Data

[63] Continuation of Ser. No. 339,190, Nov. 10, 1994, abandoned.

[30] Foreign Application Priority Data

Nov. 19, 1993 [JP] Japan .................................. 5-290452

[51] Int. Cl.$^6$ .................................................. C07K 5/075
[52] U.S. Cl. .................................................. 560/41
[58] Field of Search .................................. 560/39, 41

[56] References Cited

U.S. PATENT DOCUMENTS 5,292,923  3/1994  Kato et al. .
5,358,186  10/1994 Kataoka et al. .
5,393,915  2/1995  Kataoka et al. .

FOREIGN PATENT DOCUMENTS 0 514 936  11/1992  European Pat. Off. .

OTHER PUBLICATIONS

Chemical Engineers' Handbook 5th Ed. pp. 19–65, 19–74 and 20–24 1973.

Primary Examiner—Robert Gerstl
Attorney, Agent, or Firm—Oblon, Spivak, McClelland, Maier & Neustadt, P.C.

[57] ABSTRACT

Wet crystals of α-L-aspartyl-L-phenylalanine methyl ester with low water content can be obtained with high efficiency by solid-liquid separation of an aqueous suspension of α-L-aspartyl-L-phenylalanine methyl ester. The aqueous suspension is compressed at a final pressure of at least 20 kg/cm$^2$ as a bearing pressure, and the wet crystals are dried after compression.

7 Claims, No Drawings

PROCESS FOR PRODUCING α-L-ASPARTYL-L-PHENYLALANINE METHYL ESTER

This application is a Continuation of application Ser. No. 08/339,190, filed on Nov. 10, 1994, now abandoned.

BACKGROUND OF THE INVENTION

1. Field of the Invention

This invention relates to a process for producing α-aspartyl-L-phenylalanine methyl ester (hereinafter referred to as α-APM) by solid-liquid separation of an aqueous suspension thereof.

2. Discussion of the Background

α-APM obtained according to the present invention is useful as a low calorie dietary sweetener which is about 200 times as sweet as sugar.

The following processes are known for industrial production of α-APM:

(1) a process which comprises coupling N-protected L-aspartic anhydride with L-phenylalanine methyl ester in an organic solvent, followed by deprotection (U.S. Pat. No. 3,786,039), (2) a process wherein α-L-aspartyl-L-phenylalanine is converted to its methyl ester in a mixed solvent consisting of water, methanol and hydrochloric acid to obtain α-APM hydrochloride, which is neutralized to obtain α-APM (Japanese Patent Application Laid-open No. 82752-1978), and (3) a process which comprises condensing N-protected L-aspartic anhydride with phenylalanine methyl ester in the presence of an enzyme, followed by deprotection (Japanese Patent Publication No. 135595-1980).

Any of these processes can include a crystallization step for purification of the product. For example, in the chemical synthesis process (1) above, selective removal of impurities including the β-isomer (β-L-aspartyl-L-phenylalanine methyl ester) which is inevitably obtained as a by-product, is accomplished by contacting the crude product with a hydrohalogenic acid to crystallize the product as a hydrohalide salt. The hydrohalide salt of α-APM is obtained in the form of wet crystals and subsequently dissolved or suspended in an aqueous solvent which is neutralized by adding a base to separate α-APM as wet crystals. For further purification, the crystals of α-APM may be redissolved and recrystallized. These operations may be carried out by a continuous process or a batch process. Whether recrystallization is carried out or not the final product is usually a dried product. Such dried products are generally obtained by drying wet crystals after the last crystallization.

The aforementioned various operations for crystallization may be generally conducted in a crystallization tank accompanied with forced flow such as stirring or external circulation. When α-APM is crystallized under forced flow, it is known that the solid-liquid separation and dehydration properties of the resulting suspension are extremely poor. For example, in an industrial scale process, when the suspension (1.3 m³) obtained by cooling a 3.5 wt % solution of α-APM from 65° C. to 5° C. is separated using a centrifugal filter (diameter, 1,220 mm; height, 500 mm), it requires 2.5 hours and 2 hours for charging of the suspension and dehydration, respectively. Further, the water content of the resulting wet crystal is as high as 55–60 wt % based on the weight of wet crystals (Cf. Comparative Example 1). Longer separation time requires more separators for treatment of a specified amount of suspension, resulting in large equipment costs. Further, when the wet crystals are dried after separation, high water content results in large heat load during the drying step.

Wet crystals with high water content are very sticky and have other problems, for example, adhesion of crystals to the walls of the apparatus during the transporting and drying steps. Such problems can become severe, particularly when the wet crystals are continuously dried after separation. That is, cleaning operations to remove crystals adhering to continuous transport lines, feeders to the dryers, and internal surfaces of the dryers are required at a high frequency. Too much adhesion makes continuous operations impossible. A water content in the wet crystals of around 40% or more is considered to cause problems. As mentioned above, it is extremely difficult to reduce the water content of the wet crystals to below 50% if the water separation is carried out using a centrifugal filter. Such problems may also occur when separation is done by filtration under reduced pressure filtration, such as with a continuous belt filter or Oliver filter.

The problems to be solved by the invention are as follows:

(1) The separation time for solid-liquid separation of α-APM is too long in conventional processes;

(2) The heat load for drying is great due to high water content of the wet crystals obtained by separation; and (3) The wet crystals obtained by conventional separation processes are too sticky. Adhesion of crystals to the internal surfaces of apparatuses used during transportation and drying should be reduced.

SUMMARY OF THE INVENTION

An object of the invention is to provide a process for producing α-L-aspartyl-L-phenylalanine methyl ester by solid-liquid separation comprising: separating water from an aqueous suspension of α-L-aspartyl-L-phenylalanine methyl ester, wherein said aqueous suspension is pressed at a final pressure not less than 20 kg/cm² as a bearing pressure, and drying the wet crystals after compression.

DETAILED DESCRIPTION OF THE PREFERRED EMBODIMENTS

The present inventors have studied intensively to solve the aforementioned problems in solid-liquid separations of aqueous suspensions of α-APM. As a result, we have obtained a novel finding, that is, wet crystals with water content not more than 40% can be obtained by compression of the suspension under high pressure of not less than 20 kg/cm². The dehydration degree of the separated wet crystals becomes constant as the pressure for compression increases to about 15 kg/cm². However, in the case of α-APM, since the compressibility of the wet crystal cake is extremely high, the compression shows a significant effect under high pressure of not less than 20 kg/cm². Thus obtained wet crystal are less sticky, and a continuous drying step can be conducted over a long period of time without any problems.

In addition, when a compression pressure is set extremely high, i.e., not less than 50 kg/cm², the water content of the wet crystals is reduced to 30% or lower and the heat load during drying has been found to be significantly reduced.

It takes about 5 minutes for such compression and separation even when the thickness of the wet crystal is about 5–6 mm. Thus, the filtration area required for treatment of a specified amount of suspension can also be reduced.

In addition, it has been found that compression is effective for dehydration and removal of stickiness of the wet crystals even when the aqueous suspension of α-APM obtained by crystallization has been subjected to solid-liquid separation methods other than compression separation, and the obtained wet crystals are compressed directly or after mixing with water by kneading, resuspending or the like.

The present inventors have solved the above problems by applying these novel findings to a practical process for production of α-APM, rationalized the steps, and attained the present invention. That is, the subject invention is a process for producing α-APM by solid-liquid separation of an aqueous suspension of α-APM, wherein said aqueous suspension or wet crystals obtained by separating said aqueous suspension or a mixture of said wet crystals and water is pressed so that the final pressure for compression is not less than 20 kg/cm$^2$, and the wet crystals after pressing are dried.

The process for compression according to the present invention is not particularly limited as long as the final pressure for compression is not less than 20 kg/cm$^2$. For example, a process wherein said suspension is supplied into the gap of a double cylinder of which the inside or outside cylinder is equipped with filter cloth, and pressure is applied from the cylinder without filter cloth, or a process wherein said suspension is supplied into a cylinder covered with filter cloth on one side and pressure is applied from the other side using a piston may be employed. The pressure may be 20 kg/cm$^2$ or more from the beginning of the separation, or the separation process may be started at low pressure and after a cake is formed to some extent, the pressure may be increased to 20 kg/cm$^2$ or more. Considering the possibility of leakage of the suspended crystals into filtrate during compression, the filter cloth desirably has a plain or twilled weave and air permeability not more than 3 cc/cm$^2$ sec.

As mentioned above, compression may be conducted after an aqueous suspension of α-APM is supplied directly to a compression device. Alternatively, said aqueous suspension can be separated from water by means other than compression and the resulting wet crystals then supplied to the compression device where compression is conducted. For the purpose of, for example, increasing the flowability of the feed crystals, enhancing washing efficiency of the wet crystals or the like, the wet crystals can be supplied after kneading with water, or supplied after resuspending in water in the latter process. A suitable means for separation other than compression is, for example, continuous filtration under reduced pressure.

The thickness of the wet crystals during compression is not limited to any particular value. Considering the effect of compression and for easy removal of the wet crystals from the filter cloth, the thickness is desirably 4 mm or more at a pressure of 20 kg/cm$^2$, and 3 mm or more at a pressure of 50 kg/cm$^2$. The concentration of the suspension supplied to the compression device is not particularly limited so long as wet crystals of such thicknesses can be obtained. Even suspensions of low concentration can be employed by pre-filtration of the suspension in the device before compression by applying liquid pressure of several kilograms per cm$^2$ to the suspension when it is supplied to the device.

In some cases the wet crystals are required to be washed during the compression operation. This step can be carried out by a substitution washing operation wherein the wet crystal cake is first formed at a relatively low pressure of 10–50 kg/cm$^2$, then the inside of the separator is filled with washing liquid, subsequently the washing liquid is passed through the wet crystal cake at a relatively high pressure of 50–100 kg/cm$^2$.

When the wet crystals are dried after compression, they are desirably dried continuously considering the lower cost for construction of such an apparatus. The wet crystals obtained according to the subject invention are almost free from the problems of adhesion to the device, therefore such continuous drying process can be readily conducted. The temperature of the hot air is desirably not lower than 50° C. considering drying efficiency. The dried product can be obtained as a powder by a process involving a grinding step before or after the drying step. Alternatively, a method involving granulation affords product in the form of granules.

In the industrial process for making α-APM by solid-liquid separation of an aqueous suspension of α-APM, wet crystals with low water content and free from adhesion can be obtained according to the present invention. Accordingly, heat load during drying of the wet crystals can be considerably reduced, and drying can be conducted continuously. Further, the equipment required is reduced because of reduced time required for separation. Therefore, the present process has practical value because resources are greatly conserved.

Other features of the invention will become apparent in the course of the following descriptions of exemplary embodiments which are given for illustration of the invention and are not intended to be limiting thereof.

SUSPENSION 1

The suspension used in the following examples, hereinafter referred to as "suspension 1", was prepared as follows. A 3.5 wt % solution of α-APM (19 m$^3$, liquid temperature, 65° C.) is charged in a 21 m$^3$ stirring tank having a cooling surface, and cooled from 65° C. to 5° C. over a period of 6 hours with stirring for crystallization.

EXAMPLE 1

Suspension 1 was filtered under reduced pressure to prepare a high concentration suspension; a three-fold concentrate, hereinafter referred to as "suspension 2". Suspension 2 (180 g) was supplied to a piston-type press filter (cylinder diameter, 75 mm) wherein filtrate was extruded with a piston from one side to the opposite side of the cylinder equipped with a filter cloth. After compressing for 3 minutes at various pressures, the water content of the wet crystals was measured according to Karl Fischer's method. The results are shown in Table 1.

TABLE 1

|  | Pressure (kg/cm$^2$) | | | |
|---|---|---|---|---|
|  | 10 | 20 | 50 | 100 |
| Thickness of Wet Crystals (mm) | 5.5 | 4.0 | 3.5 | 3.0 |
| Water Content (%) | 55 | 38 | 29 | 23 |

EXAMPLE 2

Suspension 1 was separated using a Tube Press type TPM manufactured by Asizawa (filtration area, 0.9 m$^2$, charged amount, 35 L), which is an industrial compression separator. This separator, a double cylinder type device, was equipped with a filter cloth in the inside cylinder and diaphragm for compression in the outside cylinder. The suspension supplied between them was compressed from the outside cylinder.

Firstly, suspension (180 L) was supplied in the separator at a pressure of 5 kg/cm$^2$. The charged volume of the device was 35 L. That is, about 5-fold pre-concentration was completed in the separator while supplying the suspension which took 5 minutes for the supplying step.

The supplied suspension was compressed and separated at a pressure of 50 kg/cm² for 5 minutes. Subsequently, the inside cylinder was slid downwardly while wet crystals adhered to the filter cloth. Then air was blown from the inside to peel off the wet crystals. The peeling performance was good. Wet crystals of 5–6 mm thickness with average water content of 28% were obtained. The time required for peeling was 3 minutes.

Subsequently, separation operations were repeated for 12 hours in the same manner. As the result, 8.6 m³ of suspension in total could be treated which corresponds to 19.1 m³/D.m² calculated as a treated amount per unit filtration area per day. Then 140 kg (wet basis) of thus obtained wet crystals were continuously dried using a Micron Drier type MDV-1 manufactured by Hosokawa Micron. The hot air inlet temperature was set at 170°–180° C. and the drying process was conducted for 4 hours. During the process, adhesion of crystals did not become a problem in the charge hopper, screw-type feeder or drier body. Finally, 95 kg of dried crystals with water content of 2.3–2.5% were obtained. Heat load per 1 kg of the dried crystals was calculated as 238 kcal/kg including heat loss.

COMPARATIVE EXAMPLE 1

Suspension 1 was separated using a bottom discharging type centrifugal filter (basket diameter, 1,220 mm; basket height, 500 mm; filtration area, 1.9 m²). It took as long as 150 minutes to supply the suspension because the liquid was not filtered well. After the supplying step was completed, separation and dehydration operations were conducted for 120 minutes. Water content of the resulting wet crystals was as much as 55%.

Subsequently, the same separation operation was repeated and three cycles of separation were conducted. The remaining crystal layers that adhered to the clearance between scraper and filter cloth could not be scraped off in the first cycle and was consolidated thereafter. Accordingly, after the second cycle was completed, the remaining layer was removed by hand. As a result, it took 15 hours to complete three cycles in total. The total amount of the treated suspension was 3.7 m³, which is calculated to be 3.1 m³/D.m² as a treated amount per unit filtration area per day. Water content of the resulting wet crystals was 55–60 wt %.

Subsequently, 100 kg (wet basis) of thus obtained wet crystals were dried by a Micron drier type MDV-1 in the same manner as in Example 2. The wet crystals were sticky and considerably adhered to the charge hopper and screw-type feeder, making automatic supplying by these devices impossible. Therefore, the drying step was conducted by extruding the wet crystals into the dryer by manual operation. It required four hours to complete the drying steps, affording 33 kg of dried crystals with water content of 2–3%. Average heat load per 1 kg of the dried crystals was calculated as 800 kcal/kg including heat loss.

The results of Example 2 as well as Comparative Example 1 are shown in Table 2.

TABLE 2

|  | Ex. 2 | Com. Ex. 1 |
|---|---|---|
| Treated Suspension per unit filtration area (m³/D.m²) | 19.1 | 3.1 |
| Water Content of Wet Crystals (%) | 28 | 55–60 |
| Adhesion of crystals during drying step | small | significant |
| Heat load during drying step (kcal/kg) | 238 | 800 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A low-heat-load process for drying α-L-aspartyl-L-phenylalanine methyl ester by solid liquid separation comprising:

separating water from an aqueous suspension of α-L-aspartyl-L-phenylalanine methyl ester by filtering said aqueous suspension under compression which reaches a final pressure of not less than 20 kg/cm²;

and drying the wet crystals after compression.

2. A process according to claim 1, wherein the final pressure for compression is not less than 50 kg/cm².

3. A process according to claim 1, wherein the wet crystals after compression are continuously dried with hot air at a temperature not lower than 50° C.

4. A low-heat-load process for drying α-L-aspartyl-L-phenylalanine methyl ester by solid liquid separation of an aqueous suspension of α-L-aspartyl-L-phenylalanine methyl ester comprising:

obtaining wet crystals by separation of said aqueous suspension or a mixture of said wet crystals and water, and pressing the wet crystals under a final pressure of not less than 20 kg/cm²;

and drying the wet crystals after compression.

5. A process according to claim 4, wherein the final pressure for compression is not less than 50 kg/cm².

6. A process according to claim 5, wherein the wet crystals used for compression are those obtained by continuously filtering the aqueous suspension of α-L-aspartyl-L-phenylalanine methyl ester under reduced pressure.

7. A process according to claim 4, wherein the wet crystals after compression are continuously dried with hot air at a temperature not lower than 50° C.

* * * * *